United States Patent [19]
Bauer et al.

[11] Patent Number: 5,347,019
[45] Date of Patent: Sep. 13, 1994

[54] PROCESS FOR THE PREPARATION OF 4-(2-AMINOPHENYLTHIO)NAPHTHALIC ANHYDRIDE DERIVATIVES

[75] Inventors: Wolfgang Bauer, Maintal; Wassilis Koumbouris, Frankfurt am Main, both of Fed. Rep. of Germany

[73] Assignee: Cassella AG, Frankfurt, Fed. Rep. of Germany

[21] Appl. No.: 63,148

[22] Filed: May 18, 1993

[30] Foreign Application Priority Data

May 21, 1992 [DE] Fed. Rep. of Germany ....... 4216796

[51] Int. Cl.$^5$ .......................................... C07D 311/78
[52] U.S. Cl. ...................................................... 549/232
[58] Field of Search .......................................... 549/232

[56] References Cited

U.S. PATENT DOCUMENTS

| | | | |
|---|---|---|---|
| 3,850,964 | 11/1974 | Williams, III | 549/232 |
| 3,850,965 | 11/1974 | Williams, III | 549/232 |
| 3,954,810 | 5/1976 | Deucker et al. | 549/232 |
| 4,033,986 | 7/1977 | Castenson et al. | 549/232 |
| 4,086,248 | 4/1978 | Arnold et al. | 549/232 |
| 4,212,813 | 7/1980 | Hasegawa | 549/232 |
| 4,582,910 | 4/1986 | Orth et al. | 549/232 |
| 4,599,431 | 7/1986 | Schiessler et al. | 549/232 |

FOREIGN PATENT DOCUMENTS 2134517 12/1972 Fed. Rep. of Germany.
2132963 1/1973 Fed. Rep. of Germany.
2447024 11/1976 Fed. Rep. of Germany.

OTHER PUBLICATIONS

Tetrahedron, "A New Intramolecular Cyclisation Reaction–I", vol. 30, pp. 2245–2249 (1974).
J. Heterocycl. Chem. 22, "Preparation of 1,8-Naphthalimides as Candidate Fluorescent Probes", pp. 1567–1572 (1985).
Ullmanns Encyklopadie der Technischen Chemie, 4th Ed., vol. 10, pp. 449–472 (1975).
Venkataraman, The Chemistry of Synthetic Dyes, vo. III, pp. 86–90 (1974).
Dyes and Pigments 6, "Intermediates and Dyes for Synthetic-Polymer Fibres . . . ", pp. 267–275 (1985).
Journal of Heterocyclic Chemistry "Heterocyclic Derivatives of Naphthalene-1,8-dicarboxylic Anhydride", P. H. Grayshan et al., Feb. 1974, vol. 11, pp. 33–38.

*Primary Examiner*—C. Warren Ivy
*Assistant Examiner*—A. A. Owens
*Attorney, Agent, or Firm*—Connolly & Hutz

[57] ABSTRACT

4-(2-Aminophenylthio)naphthalic anhydride derivatives are obtained in good yields and purities by reaction of 2-aminothiophenolates with 4-chloro- or 4-bromonaphthalic anhydrides having a particle size of at most 50 μm.

23 Claims, No Drawings

PROCESS FOR THE PREPARATION OF 4-(2-AMINOPHENYLTHIO)NAPHTHALIC ANHYDRIDE DERIVATIVES

The present invention relates to a process for the preparation of 4-(2-aminophenylthio)naphthalic anhydride derivatives of the formula I

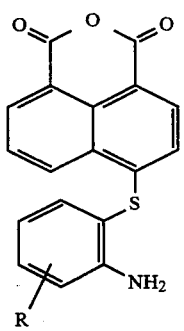

in which R denotes H, methyl, ethyl, methoxy, ethoxy or chlorine.

The compounds of the formula I are important intermediates which are required, for example, for the preparation of fluorescent dyes, cf., for example, German Patent Specifications 2,447,024, 2,132,963, 2,134,517 and A. T. Peters et al., Tetrahedron 30, 2245 (1974). In order to be suitable for the preparation of fluorescent dyes of this type without further purification operations, the compounds of the formula I must have a high purity.

Various nucleophilic exchange reactions of 4-halonaphthalic anhydride derivatives with alkali metal thiolates are already known for the preparation of naphthalic anhydride derivatives substituted in the 4-position by alkyl or arylthio radicals. A common feature of these known processes is that yields and/or purities are unsatisfactory and that they moreover have to be carried out in organic solvents, as a result of which considerable costs result for the recovery of the solvents or the waste-water purification.

According to P. H. Grayshan et al., J. Heterocycl. Chem. 11, 33–38 (1974), the reaction of 4-chloronaphthalic anhydride with 2-aminothiophenol and potassium carbonate is carried out in dimethylformamide. In this reaction, however, undesired side reactions take place, so the resulting by-products have to be removed by complicated, cost-intensive purification operations. The yield of 4-(2-aminophenylthio)naphthalic anhydride by this process is only about 60% of theory. Apart from the poor yield and the production of undesired by-products, this process is economically disadvantageous due to the production of a filtrate of aqueous dimethylformamide, as a result of which high technical expenditure due to solvent regeneration and waste-water purification measures is necessary. The use of 2-methoxyethanol gives similar results to those with dimethylformamide; the reaction proceeds incompletely in ethanol, associated with the formation of large amounts of undesired 2,2-diaminodiphenyl disulphide.

A yield of only 72% of theory is also obtained in the reaction of 4-chloronaphthalic anhydride with 1-butanethiol and potassium carbonate in dimethylformamide (R. W. Middleton et al., J. Heterocycl. Chem. 22, 1567–1572 (1985)). In this process too, by-product formation and production of aqueous dimethylformamide result in high costs with respect to disposal of by-products, solvent regeneration and protection of rivers, lakes and canals.

The reaction of 4-chloro-3-nitronaphthalic anhydride with thiophenol carried out in ethanol as a solvent according to A. Peters et al., Dyes and Pigments 6, 267–275 (1985) yields 3-nitro-4-phenylthionaphthalic anhydride in a yield of 57% of theory. In this process too, complicated and cost-intensive methods are necessary in order to avoid pollution of the environment.

The reactions of 4-halonaphthalic anhydrides with alkali metal thiophenolates described in U.S. Pat. No. 3,850,965 are carried out, for example, in dimethylformamide or dimethyl sulphoxide and benzene with removal of water by distillation. In this process too, the disadvantage already described occur. In addition, there is also a high health risk due to the use of benzene.

The object of the present invention was therefore to indicate a process for the preparation of the 4-(2-aminophenylthio)naphthalic derivatives of the formula I by reaction of 4-halonaphthalic anhydrides of the formula II

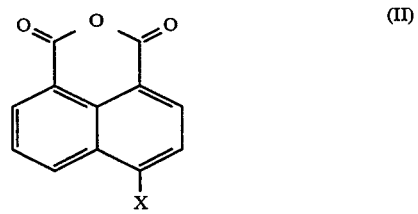

in which X denotes chlorine or bromine, with 2-aminothiophenolates of the formula III

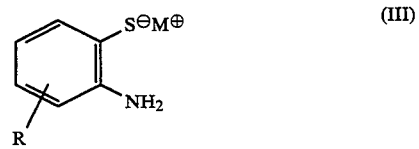

in which R has the meaning already mentioned and M⊕ denotes an alkali metal cation, the ammonium ion or a substituted ammonium ion, which does not have the disadvantages of the previously known processes, but nevertheless permits the compounds of the formula I to be prepared in substantially better yields and purities without the production of undesired by-products.

The object set is achieved as in the claims.

Surprisingly, it has been found that in the reaction of a 4-halonaphthalic anhydride of the formula II with a 2-aminothiophenolate of the formula III, the compound of the formula I is obtained in substantially better yield and purity if the 4-halonaphthalic anhydride of the formula II employed has a maximum particle size of about 50 μm. Preferably, the 4-halonaphthalic anhydride of the formula II employed has a maximum particle size of about 40 μm and very particularly preferably of about 25 μm.

The 4-halonaphthalic anhydride employed is preferably 4-chloronaphthalic anhydride, i.e. in the formula II, X preferably denotes chlorine.

In the formula III, R preferably denotes hydrogen. An alkali metal cation is preferred for M⊕. Alkali metal cations which can be mentioned are, for example, the lithium, sodium, potassium, rubidium or caesium cation, of which the lithium, sodium and potassium cations are preferred. M⊕ can also be the ammonium ion NH₄⊕ or a substituted ammonium ion. Substituted ammonium ions are, for example, those in which one, two or three hydrogen atoms of the ammonium ion NH₄⊕ are replaced by identical or different alkyl radicals having 1 to 4 C atoms and/or by identical or different alkanol radicals having 2 to 4 C atoms. Substituted ammonium ions of this type are derived, for example, from mono-, di- or trialkylamines, such as, for example, mono-, di- and triethylamine, isopropylamine, di-n-propylamine, iso-butylamine, methylethylamine or from mono-, di- and trialkanolamines, such as, for example, ethanolamine, diethanolamine, triethanolamine or dimethylethanolamine. Instead of employing an alkali metal or ammonium 2-aminothiophenolate of the formula III, the alkali metal or ammonium 2-aminothiophenolate can also be allowed to form in the reaction, i.e. the appropriate 2-aminothiophenol (in which M denotes H in formula III), for example, can be employed in combination with an alkali metal carbonate, bicarbonate or hydroxide or an amine or alkanolamine.

The process according to the invention is carried out in a suitable solvent or solvent mixture. Suitable solvents are, for example, alcohols, in particular ethanol, glycols, such as ethylene glycol, di- and polyglycols, such as, for example, diethylene glycol, triethylene glycol, glycol ethers, such as, for example, methyl glycol, butyl glycol, methyl diglycol, ethylene glycol dimethyl ether, urea derivatives, such as, for example, tetramethylurea, acid amides, such as, for example, dimethylformamide, N-methylpyrrolidone, or sulphoxides, such as, for example, dimethyl sulphoxide. Water in a mixture with one or more partially or completely water-miscible solvents, for example, can be used as a solvent mixture. Examples of suitable partially or completely water-miscible solvents are listed above. However, since the process according to the invention surprisingly also gives excellent results in water, it is preferred to carry out the process according to the invention in water without the addition of organic solvents in order to avoid the disadvantages caused by the organic solvent, for example as a result of solvent regeneration or waste-water treatment.

The reaction according to the invention can be carried out, for example, at a temperature from about 30 to about 150° C., preferably from about 50° to about 90° C. The molar ratio compound II: compound III in the reaction is preferably 1:(1 to 1.5).

In the preparation of the 4-halonaphthalic anhydrides of the formula II, these compounds are obtained with particle sizes up to 100 μm and more. The starting materials of the formula II having maximum particle sizes of about 50 μm which are required for the process according to the invention can be prepared from products of this type in a manner known per se by dry or wet particle comminution. Comminution processes of this type can be carried out, for example, in suitable grinding or dispersing devices known per se, for example sand mills, bead mills, or by the use of ultrasound.

It is advantageous to carry out the comminution in a liquid, in particular aqueous, medium and at the same time to prepare a liquid, in particular aqueous, dispersion having maximum particle sizes of about 50 μm, preferably about 40 μm and very particularly preferably about 25 μm, and to employ the starting material II in the form of this liquid, in particular aqueous, dispersion in the process according to the invention.

When carrying out the comminution or dispersion process, it is advantageous to add one or more surfactants known per se to the compounds of the formula II to be dispersed in a liquid, in particular in an aqueous medium, preferably in water. Suitable surfactants come, for example, from the group comprising the anionic and non-ionic surfactants and are employed, for example, in an amount from 0.001% to 1% by weight, relative to the compound of the formula II. A survey of suitable non-ionic or anionic surfactants can be found, for example, in Ullman, "Enzyklopadie der Technischen Chemie" (Encylopaedia of Industrial Chemistry), 4th Edition, Volume 10, page 449 ff., and Volume 22, page 455 ff., or in E. H. Daruwalla in K. Venkataraman "The Chemistry of Synthetic Dyes", Vol. VII, pages 86 to 92 (1974).

Examples of particularly suitable anionic surfactants are: ligninsulphonate, alkanesulphonates, olefinsulphonates, ester sulphonates, alkylarylsulphonates, alkylsulphonates, ether sulphates, fatty alcohol sulphates and phenolsulphonic acid/formaldehyde and naphthalenesulphonic acid/formaldehyde condensation products.

Particularly preferred non-ionic surfactants are derived from the series comprising the alkylphenol polyglycol ethers and their condensation products with phenol and formaldehyde as well as the ethoxylation products of fatty acids, fatty acid amides, fatty amines and fatty alcohols.

The use of a preferably aqueous dispersion of the starting material of the formula II having a maximum particle size of about 50 μm, preferably about 40 μm and particularly preferably about 25 μm, which preferably contains a surfactant or several surfactants, is a particularly preferred embodiment of the process according to the invention.

A dispersion of the starting material of the formula II can either be added, in particular metered in, to a preferably aqueous solution of the 2-aminothiophenolate of the formula III, or the dispersion of the starting material of the formula II is added, in particular metered in, to an, in particular aqueous, solution of 2-aminothiophenolate of the formula III.

Even if the 4-halonaphthalic anhydride of the formula II is not employed in the form of a dispersion containing a surfactant, it may be advantageous to carry out the process according to the invention in the presence of a surfactant or several surfactants. The surfactants already mentioned in the amounts already mentioned are also suitable for this purpose.

The process according to the invention is carried out in an aqueous medium, in particular at a pH from about 4 to about 10, preferably at a pH from about 5 to about 9.

The required starting compounds of the formulae II and III are known or can be prepared by synthesis processes known for these classes of compound.

The process according to the invention, in which the use of organic solvents and working in water-free medium can be dispensed with, yields 4-(2-aminophenylthio)naphthalic anhydrides of the formula I in surprisingly high yields of up to 95% of theory and in such a high purity that they can be employed directly without further purification operations as starting materials in the synthesis of fluorescent dyes.

In comparison to the already known processes, the process according to the invention offers distinct advantages, in particular with respect to yield and purity of the products, and with respect to economy and environmental protection.

In the Examples below, percentage data denote percentages by weight.

EXAMPLE 1

A mixture of 232.6 g of 4-chloronaphthalic anhydride and 1 g of ligninsulphonate in 2.5 l of water is ground at 25° C. with recirculation for 30 minutes in a laboratory mill of the type PUC-RD1 (manufacturer: Probst & Class in 7550 Raststatt, Germany).

A particle size analysis (measuring method: suspension cell, ultrasound, time 15 sec) shows that particles of about 0.18 to about 20.6 μm are present in the suspension obtained. The maximum of the distribution curve is at about 2.5 μm.

706 g of a 25% strength aqueous sodium 2-aminothiophenolate solution having a pH of 9 are added at 25° C. to the finely particulate dispersion obtained, which has a pH of 5.

The reaction mixture is then heated to 80° C. and subsequently stirred at 80° C. for 2 hours.

The yellow product suspension (pH: 6) is filtered, washed with water and dried at 100° C.

Yield: 316 g of yellow crystals of 4-(2-aminophenylthio)naphthalic anhydride having a purity determined by diazotisation of 96%, corresponding to a yield relative to 4-chloronaphthalic anhydride employed of 94.4% of theory.

Melting point: 196° to 199° C.

The product obtained is outstandingly suitable for the synthesis of fluorescent dyes without further purification operations.

COMPARISON EXAMPLE 232.6 g of the 4-chloronaphthalic anhydride also used in Example 1 are introduced into a mixture of 1 g of lignin sulphonate and 1535 ml of water. The suspension obtained is then stirred at 25° C. for 30 minutes. A particle size analysis (measuring method: suspension cell; ultrasound, time 15 sec) shows that 40% of the particles have a size from 20 to 100 μm.

The suspension obtained is then reacted with 706 g of a 25% strength aqueous sodium 2-aminothiophenolate solution according to the details of Example 1.

Yield: 301.4 g of yellow powder having a purity of 80% of 4-(2-aminophenylthio)naphthalic anhydride corresponding to 75% of theory, relative to 4-chloronaphthalic anhydride employed. Melting point: 168° to 176° C.

The product is not suitable for the preparation of fluorescent dyes without further purification operations.

Further examples of the process according to the invention which are carried out according to Example 1, can be taken from the following table, starting materials of the formula II being given in column 2, starting materials of the formula III in column 3, the surfactant employed in column 4, the maximum particle size in column 5, the solvent employed in column 6 and the yield of the products of the formula I, relative to the starting materials of the formula II, in column 7.

The products obtained in Examples 2 to 11 are outstandingly suitable for the preparation of fluorescent dyes without further purification operations.

| Example | Starting material of the formula II X = | Starting material of the formula III M⊕ | R | Surfactant employed | Particle size max. (μm) | Solvent | Yield in % of theory | Purity |
|---|---|---|---|---|---|---|---|---|
| 2 | Br | Li⊕ | H | ®Tamol NNC 1) | 30 | Water | 92 | 97 |
| 3 | Cl | K⊕ | H | ®Hostapur SAS 93 2) | 40 | Water | 89 | 95 |
| 4 | Cl | Na⊕ | 3-CH₃ | Ligninsulphonate | 20 | Watar | 90 | 96 |
| 5 | Cl | Na⊕ | 5-Cl | Ligninsulphonate | 20 | Water | 88 | 96 |
| 6 | Cl | Na⊕ | 2-OC₂H₅ | Ligninsulphonate | 20 | Water | 87 | 94 |
| 7 | Cl | Na⊕ | H | Emulsifier W 3) | 20 | Water | 90 | 96,5 |
| 8 | Cl | Na⊕ | H | Ligninsulphonate | 20 | Water/ethanol (Wt. ratio 1:1) | 87 | 96 |
| 9 | Cl | NH₄⊕ | H | Ligninsulphonate | 25 | Water | 91 | 95 |
| 10 | Cl | HN⊕(C₂H₅)₃ | H | Ligninsulphonate | 20 | Water | 90 | 98 |
| 11 | Cl | H₂N⊕(C₂H₄OH)₂ | H | Ligninsulphonate | 20 | Water | 89 | 98 |

1) Commercial product of BASF AG, Ludwigshafen, Germany, based on naphthalenesulphonate/formaldahyde
2) Commercial product of HOECHST AG, Frankfurt/Main, Germany; secondary alkanesulphonate;
3) Commercial product of BAYER AG, Leverkusen, Germany; aryl polyglycol ether.

We claim:

1. Process for the preparation of 4-(2-aminophenylthio)naphthalic anhydride derivatives of the formula I

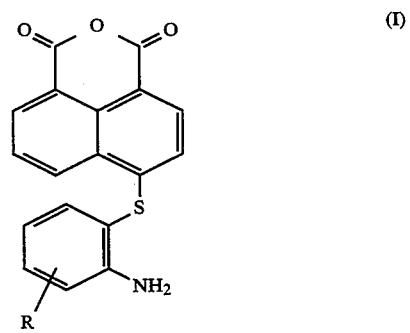

in which R denotes H, methyl, ethyl, methoxy, ethoxy or chlorine, comprising reacting 4-halonaphthalic anhydrides of the formula II

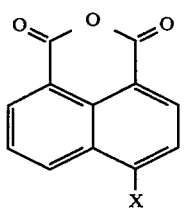

in which X denotes chlorine or bromine, with 2-aminothiophenolates of the formula III

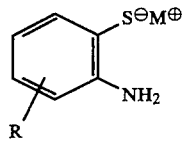

in which R has the meaning mentioned above and $M^\oplus$ is selected from the group consisting of an alkali metal cation, ammonium ion and a substituted ammonium ion; wherein said 4-halonaphthalic anhydride of the formula II employed has a maximum particle size of about 50 μm.

2. Process according to claim 1, wherein the 4-halonaphthalic anhydride of the formula II has a maximum particle size of about 40 μm.

3. Process according to claim 2, wherein the 4-halonaphthalic anhydride of the formula II has a maximum particle size of about 25 μm.

4. Process according to claim 1, wherein
a) X denotes chlorine,
b) R denotes hydrogen,
c) $M^\oplus$ denotes an alkali metal cation, any combination of a), b), and c).

5. Process according to claim 4, wherein said alkali metal cation is selected from the group consisting of lithium, sodium and potassium cation.

6. Process according to claim 1, wherein the reaction is carried out at a temperature from about 30° to about 150° C.

7. Process according to claim 3, wherein
the reaction is carried out at a temperature from about 50° to about 90° C. and
the molar ratio between the said compound II and said compound III is 1: (1 to 1.5).

8. Process according to claim 1, wherein the 4-halonaphthalic anhydride of the formula II is employed in the form of a liquid.

9. Process according to claim 8, wherein said liquid is an aqueous dispersion.

10. Process according to claim 9, wherein said aqueous dispersions contain at least one surfactant.

11. Process according to claim 1, wherein the reaction is carried out in the presence at least one surfactant.

12. Process according to claim 1, wherein the reaction is carried out in a mixture of water and at least one partially or completely water miscible solvent.

13. Process according to claim 1, wherein the reaction is carried out in water.

14. Process according to claim 1, wherein the reaction is carried out at a pH from about 4 to about 10.

15. Process according to claim 7, wherein the reaction is carried out at a pH from about 5 to about 9.

16. Process according to claim 1, wherein at least about 87% of formula I is produced.

17. Process according to claim 16, wherein the reaction produces compounds of formula I having a high purity without the production of undesired by-products.

18. Process according to claim 1, wherein $M^\oplus$ is an ammonium ion of the formula

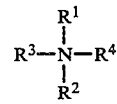

wherein $R^1$, $R^2$, $R^3$ and $R^4$ can be the same or different and are selected from the group consisting of alkyls having 1 to 4 carbon atoms, alkanols having 2 to 4 carbon atoms, and hydrogen.

19. Process according to claim 1, wherein the reaction is carried out in a solvent that is selected from the group consisting of alcohols, glycols, glycol ethers, urea derivatives, acid amides and sulphoxides or mixtures thereof.

20. Process according to claim 10, wherein the surfactant is either anionic or non-ionic or a mixture thereof.

21. Process according to claim 20, wherein said anionic surfactants are selected from the group consisting of ligninsulphonate, alkylarylsulphonates, olefinsulphonates, ester sulphonates, alkylarulsulphonates, alkylsulphonates, ether sulphates, fatty alcohol sulphates, phenolsulphonic acid/formaldehyde and naphthalenesulphonic acid/formaldehyde condensation products.

22. Process according to claim 20, wherein said non-ionic surfactants are selected from the group consisting of alkylphenol polyglycol ethers and their condensation products with phenol and formaldehyde, ethoxylation products of fatty acids, fatty acid amides, fatty amines and fatty alcohols.

23. The process according to claim 1, wherein the particle size is from about 0.18 to about 20.6 μm.

* * * * *